(12) United States Patent
Gattupalli et al.

(10) Patent No.: US 10,753,646 B2
(45) Date of Patent: Aug. 25, 2020

(54) REACTOR AND HEATER CONFIGURATION SYNERGIES IN PARAFFIN DEHYDROGENATION PROCESS

(71) Applicant: UOP LLC, Des Plaines, IL (US)

(72) Inventors: Rajeswar Gattupalli, Buffalo Grove, IL (US); Quan Yuan, Buffalo Grove, IL (US); Clayton C. Sadler, Arlington Heights, IL (US); Michael J. Vetter, Schaumburg, IL (US); Bryan J. Egolf, Crystal Lake, IL (US)

(73) Assignee: UOP LLC, Des Plaines, IL (US)

( * ) Notice: Subject to any disclaimer, the term of this patent is extended or adjusted under 35 U.S.C. 154(b) by 211 days.

(21) Appl. No.: 15/799,873

(22) Filed: Oct. 31, 2017

(65) Prior Publication Data

US 2018/0051912 A1 Feb. 22, 2018

Related U.S. Application Data

(63) Continuation of application No. PCT/US2016/038703, filed on Jun. 22, 2016.
(Continued)

(51) Int. Cl.
*F24H 9/18* (2006.01)
*F24H 1/40* (2006.01)
(Continued)

(52) U.S. Cl.
CPC ............ *F24H 9/1836* (2013.01); *B01J 8/062* (2013.01); *B01J 8/087* (2013.01); *B01J 19/2415* (2013.01);
(Continued)

(58) Field of Classification Search
CPC . F24H 9/1836; F24H 1/40; B01J 8/087; B01J 19/2415; B01J 19/2425; B01J 8/062;
(Continued)

(56) References Cited

U.S. PATENT DOCUMENTS

| 4,986,222 A | 1/1991 | Pickell et al. |
| 5,247,907 A | 9/1993 | Lee et al. |

(Continued)

FOREIGN PATENT DOCUMENTS

| CN | 201885569 U | 6/2011 |
| EP | 0134335 A1 | 3/1985 |

(Continued)

OTHER PUBLICATIONS

Search Report dated Oct. 13, 2016 for corresponding PCT Application No. PCT/US2016/038703.
(Continued)

*Primary Examiner* — Randy Boyer
*Assistant Examiner* — Juan C Valencia
(74) *Attorney, Agent, or Firm* — Paschall & Associates, LLC; James C. Paschall

(57) ABSTRACT

An apparatus for heating a process fluid is presented. The apparatus is for improving the foot-print of a fired heater and to reduce the fired heater volume. The apparatus includes a W-shaped process coil to provide for a smaller single-cell fired heater, and a fired heater with a lower profile, providing flexibility in positioning relative to downstream reactors.

19 Claims, 2 Drawing Sheets

Related U.S. Application Data

(60) Provisional application No. 62/186,781, filed on Jun. 30, 2015.

(51) Int. Cl.
  B01J 8/06 (2006.01)
  B01J 8/08 (2006.01)
  B01J 19/24 (2006.01)
  C10G 9/20 (2006.01)
  C07C 5/32 (2006.01)

(52) U.S. Cl.
  CPC ......... B01J 19/2425 (2013.01); C10G 9/203 (2013.01); F24H 1/40 (2013.01); *B01J 2208/00132* (2013.01); *B01J 2219/00083* (2013.01); *B01J 2219/00157* (2013.01); *C07C 5/32* (2013.01); *C10G 2300/1037* (2013.01); *C10G 2300/1085* (2013.01)

(58) Field of Classification Search
  CPC .... B01J 2219/00083; B01J 2219/00157; B01J 2208/00132; C10G 9/203; C10G 2300/1085; C10G 2300/1037; C07C 5/32
  See application file for complete search history.

(56) References Cited

U.S. PATENT DOCUMENTS

| | | | |
|---|---|---|---|
| 5,878,699 A | 3/1999 | Barnett et al. | |
| 6,178,926 B1 | 1/2001 | Worman | |
| 6,237,545 B1 | 5/2001 | Barnett et al. | |
| 7,687,042 B2 | 3/2010 | An et al. | |
| 8,323,365 B2 | 12/2012 | Drnevich et al. | |
| 8,490,581 B2 | 7/2013 | Chhotray et al. | |
| 2008/0142411 A1* | 6/2008 | Barendregt | C10G 9/20 208/132 |
| 2010/0243521 A1 | 9/2010 | Peters | |
| 2014/0045133 A1 | 2/2014 | Myszka et al. | |
| 2014/0323781 A1 | 10/2014 | Hartman et al. | |
| 2016/0097002 A1* | 4/2016 | Sundaram | C10G 9/36 585/324 |

FOREIGN PATENT DOCUMENTS

| | | |
|---|---|---|
| EP | 0757585 A1 | 2/1997 |
| JP | 2011234855 A | 11/2011 |
| RU | 2064823 C1 | 8/1996 |

OTHER PUBLICATIONS

Garg, "Get the most from your fired heater", originally appearing in Chemical Engineering, vol. 111, Issue 3, Mar. 2004, pp. 60-64.
Esteem, "Modular Construction of Fired Heaters", Esteem website.
Foster Wheeler, "Fired Heaters", Foster Wheeler's website.
U.S. Appl. No. 15/799,895, filed Oct. 31, 2017.
Indian First Examination Report dated Dec. 30, 2019 for corresponding IN Application No. 201717037387.
Indian First Examination Report dated Aug. 26, 2019 for corresponding IN Application No. 201717038234.

\* cited by examiner

REACTOR AND HEATER CONFIGURATION SYNERGIES IN PARAFFIN DEHYDROGENATION PROCESS

CROSS-REFERENCE TO RELATED APPLICATIONS

This application is a Continuation of International Application No. PCT/US2016/038703 filed Jun. 22, 2016 which application claims benefit of U.S. Provisional Application No. 62/186,781 filed Jun. 30, 2015, the contents of which cited applications are hereby incorporated by reference in their entirety.

FIELD OF THE INVENTION

The present invention relates to fired heaters for use in process involving chemical reactions.

BACKGROUND

Fired heaters are common process units in chemical plants. The fired heaters heat process streams to reaction temperatures, and provide heat to process streams that have endothermic reactions. A fired heater has a general configuration of a tube for carrying a process fluid inside a shell wherein burners are used to combust a fuel to heat the tubes.

With more complex processes, and with upgrades to processes in chemical plants, new configurations are needed to reduce the area taken up by fired heaters, and to provide for new efficiencies in the heating of process fluids.

Different processes have different needs from fired heaters, and these different needs can affect the designs to produce improved fired heaters that have a significant economic impact.

SUMMARY

The present invention is an improved fired heater design and integration with downstream reactors.

A first embodiment of the invention is an apparatus for reducing hot transfer volume, comprising a radiant fired heater having a single cell, at least one process coil, burners, and a flue gas outlet; and at least one outlet manifold having an inlet in fluid communication with the process coils outlets and at least one manifold outlet; wherein each process coil has a configuration of three tubes in a parallel orientation, with two semi-circular tubular sections connecting the ends of the tubes, such that the tubes and tubular sections form a generalized W-shaped coil, with the central tube having one end connected to the outlet port, and the two outer tubes having one end connected to an inlet port. An embodiment of the invention is one, any or all of prior embodiments in this paragraph up through the first embodiment in this paragraph further comprising a convection bank having an inlet in fluid communication with the flue gas outlet, and heating tubes, wherein the heating tubes have an inlet and an outlet. An embodiment of the invention is one, any or all of prior embodiments in this paragraph up through the first embodiment in this paragraph, wherein the convection bank is below the fired heater. An embodiment of the invention is one, any or all of prior embodiments in this paragraph up through the first embodiment in this paragraph, wherein the convection bank is positioned to the side of the fired heater. An embodiment of the invention is one, any or all of prior embodiments in this paragraph up through the first embodiment in this paragraph, wherein the heating tubes are for steam generation. An embodiment of the invention is one, any or all of prior embodiments in this paragraph up through the first embodiment in this paragraph further comprising a moving bed reactor having a process stream inlet located above the reactor moving bed, a process fluid outlet, a catalyst inlet, a catalyst collector at the bottom of the reactor, and a catalyst outlet at the bottom of the catalyst collector. An embodiment of the invention is one, any or all of prior embodiments in this paragraph up through the first embodiment in this paragraph, wherein the radiant fired heater is elevated to provide for that the moving bed reactor process stream inlet is located within 0.3 m elevation of the outlet manifold outlet. An embodiment of the invention is one, any or all of prior embodiments in this paragraph up through the first embodiment in this paragraph further comprising a moving bed reactor having a process stream inlet located below the reactor moving bed, a process fluid outlet, a catalyst inlet, and a catalyst outlet at the bottom of the reactor; and a catalyst collector having an inlet in fluid communication with the reactor catalyst outlet and a catalyst collector outlet. An embodiment of the invention is one, any or all of prior embodiments in this paragraph up through the first embodiment in this paragraph wherein the moving bed reactor is elevated to have the process stream inlet located within 1 m elevation of the manifold outlet. An embodiment of the invention is one, any or all of prior embodiments in this paragraph up through the first embodiment in this paragraph, wherein the moving bed reactor is elevated to have the process stream inlet located within 2 m elevation of the manifold outlet. An embodiment of the invention is one, any or all of prior embodiments in this paragraph up through the first embodiment in this paragraph further comprising a convection bank having an inlet in fluid communication with the flue gas outlet, and heating tubes, wherein the heating tubes have an inlet and an outlet. An embodiment of the invention is one, any or all of prior embodiments in this paragraph up through the first embodiment in this paragraph, wherein the convection bank is below the fired heater. An embodiment of the invention is one, any or all of prior embodiments in this paragraph up through the first embodiment in this paragraph, wherein the convection bank is positioned to the side of the fired heater.

A second embodiment of the invention is an apparatus integrated with a reactor, comprising a moving bed reactor having a process stream inlet located at a designed elevation, a process fluid outlet, a catalyst inlet, a catalyst collector at the bottom of the reactor, and a catalyst outlet at the bottom of the catalyst collector, wherein the process stream inlet is located above the moving bed and a fired heater having at least one process coil, and a flue gas outlet, wherein the process coil has at least one inlet and one outlet, and wherein the process coil outlet is located within 1 m elevation of the moving bed reactor process stream inlet designed elevation. An embodiment of the invention is one, any or all of prior embodiments in this paragraph up through the second embodiment in this paragraph further comprising a convection bank having an inlet in fluid communication with the fired heater flue gas outlet, wherein the convection bank comprises heating tubes having an inlet and an outlet. An embodiment of the invention is one, any or all of prior embodiments in this paragraph up through the second embodiment in this paragraph further comprising an outlet manifold having multiple inlets with each inlet in fluid communication with a process coil outlet, and an outlet in fluid communication with the moving bed reactor process stream inlet, and wherein the manifold outlet is located at an elevation within 0.3 m of the moving bed reactor process stream inlet. An embodiment of the invention is one, any or all of prior embodiments in this paragraph up through the second embodiment in this paragraph wherein the convection bank is located below the fired heater, or to the side of the fired heater.

A third embodiment of the invention is an apparatus integrated with a reactor, comprising a moving bed reactor having a process stream inlet located at a designed elevation, a process fluid outlet, a catalyst inlet, and a catalyst outlet at the bottom of the reactor, wherein the process stream inlet is located below the moving bed a catalyst collector having an inlet in fluid communication with the reactor outlet and an outlet; and a fired heater having at least one process coil, and a flue gas outlet, wherein the process coil has at least one inlet and one outlet, and wherein the process coil outlet is located within 1 m elevation of the moving bed reactor process stream inlet designed elevation. An embodiment of the invention is one, any or all of prior embodiments in this paragraph up through the third embodiment in this paragraph further comprising an outlet manifold having multiple inlets with each inlet in fluid communication with a process coil outlet, and an outlet in fluid communication with the moving bed reactor process stream inlet, and wherein the manifold outlet is located at an elevation within 0.3 m of the moving bed reactor process stream inlet. An embodiment of the invention is one, any or all of prior embodiments in this paragraph up through the third embodiment in this paragraph further comprising a convection bank having an inlet in fluid communication with the fired heater flue gas outlet, wherein the convection bank comprises heating tubes having an inlet and an outlet.

Other objects, advantages and applications of the present invention will become apparent to those skilled in the art from the following detailed description and drawings.

DETAILED DESCRIPTION

Chemical processes frequently need heating. Process heaters are designed to heat feed streams or intermediate process streams to temperatures necessary for the chemical reactions in the processes to occur at a reasonable rate. Process heaters can be single-cell or dual-cell and are equipped with different shapes of coils like "U-shaped" that allow for a process fluid to be heated. The coils are mounted in fired heaters that include burners. A fired heater is typically a box-shaped furnace with the coils inside the box and burners mounted on the sides or bottoms of the furnace. For a commercial process, a fired heater can be a very large item. The fired heaters can be as much as 25% of the equipment cost, and improvements in the designs to reduce costs are important.

Fired process heaters often cause non-selective reactions, such as thermal conversion or cracking of hydrocarbons. These non-selective reactions reduce yields and increase losses. Redesigned heaters can reduce these losses and proved for more desirable capital cost, operation costs and reduced area, or smaller plot space, required for a heater.

Single-cell or dual-cell fired heaters equipped with U-shaped process coils, and end-wall mounted horizontal round-flame burners are widely used in processes, such as dehydrogenation and reforming. In dehydrogenation processes, the reactions include many undesired reactions. An estimated 30% to 40% of the non-selectivity is caused by thermal cracking in the fired heaters. Redesign of the heaters can reduce the amount of these non-selective reactions, in addition to reducing capital cost and the footprint, or area, occupied by the fired heaters.

Figure 1A:
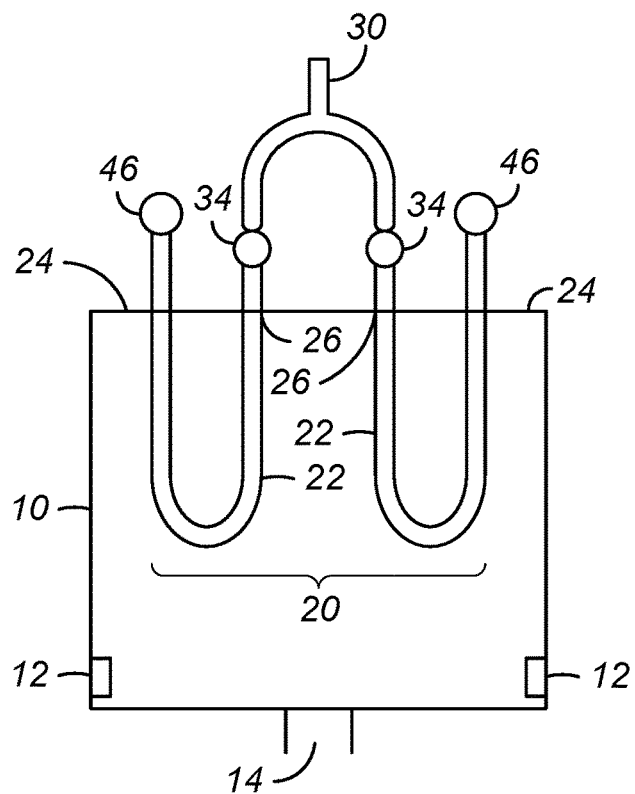
FIG. 1a is a cross-section of a fired heater with a double U-shaped process coil.
Figure 1B:
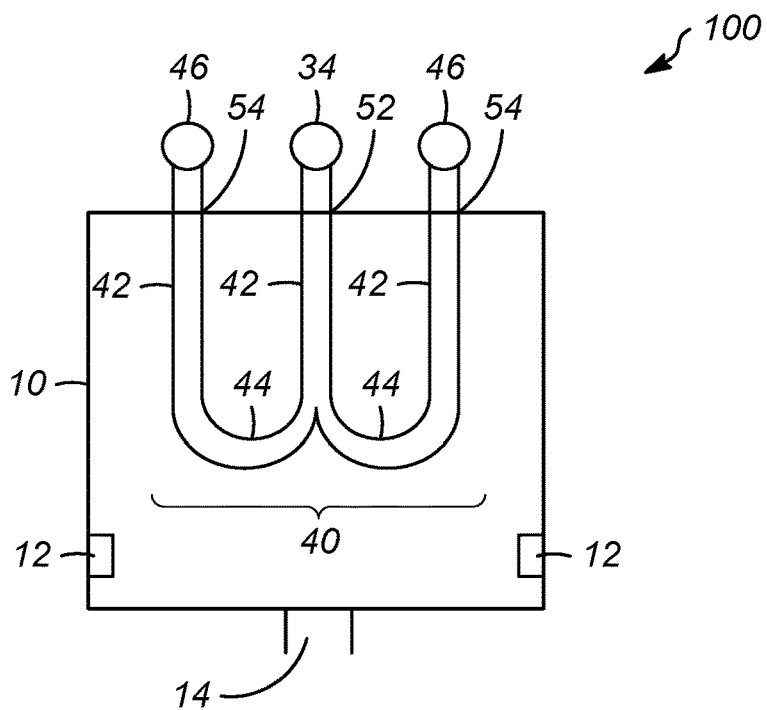
FIG. 1b is a cross-section of a fired heater of the present invention with a W-shaped process coil.

The present invention includes a single-cell fired heater 100 with a new coil configuration. A typical configuration is shown in FIG. 1a, wherein a cross-section shows the shell 10, a process coil 20 comprising two U-shaped tubes 22, burners 12, and a flue gas outlet 14. The typical configuration has two process tube inlets 24 and two process tube outlets 26. The two process tube outlets 26 pass the process fluid to separate outlet manifolds 34, and a Y-shaped connector 30 is connected to an outlet manifold 34, which merges the process fluids from the outlet manifolds 34. An embodiment of the present invention is shown in FIG. 1b, wherein the cross-section shows the shell 10, a process coil 40, burners 12 and a flue gas outlet 14. The process coil 40 has a configuration of three tubes 42 in a substantially parallel orientation with two curved sections 44 connecting the ends of the tubes 42. The curved sections can be semi-circular sections of tubing. The sections are connected to form a generalized W-shaped coil. The central tube having one end connect to an outlet port 52 and the outer tubes having one end connected to an inlet port 54. In one embodiment, to allow for constant flow velocity, the central tube has a larger diameter over the outer tubes. The flue gas outlet 14 can be located on the upper surface, or the lower surface of the shell 10.

The fired heater is in fluid communication with at least one inlet manifold 46 and one outlet manifold 34. The inlet manifold 46 brings the process fluid to be heated to the fired heater, and has a plurality of outlets, wherein each outlet is in fluid communication with a process coil inlet 24. A transfer line connecting the outlet manifold 34 carries the heated process fluid to a downstream reactor, and the outlet manifold 34 has a plurality of inlets with each inlet in fluid communication with a process coil outlet 26.

The use of the W-shaped tube allows for a much narrower fired heater allows for the elimination of the Y-shaped connector 30, which reduces the transfer line volume for the process fluid to travel from the heater to a downstream unit, or typically a reactor. Reducing the transfer line volume helps in reducing the thermal cracking in the lines leading up to the reactor. This allows for a more compact spacing of process heaters, and for better positioning of the process heaters with respect to downstream reactors. In one embodiment, the smaller fired heater allows for elevating or positioning the fired heater to make use of the hot flue gases. The hot flue gases that exit the fired heater outlet 14 have temperatures in the range of 700° C. to 1100° C., and are passed to a convection bank. The convection bank includes heating tubes for steam generation, or for other means of heat recovery.

The present invention is an integration of a fired heater with existing reactors to improve the transfer of process fluids from the fired heater to a downstream reactor, and to recover heat from the fired heater flue gas. By removing the Y-shaped connector 30, the fired heater can be positioned closer to the reactor minimizing the transfer lines between the fired heater and downstream reactors.

Figure 2:
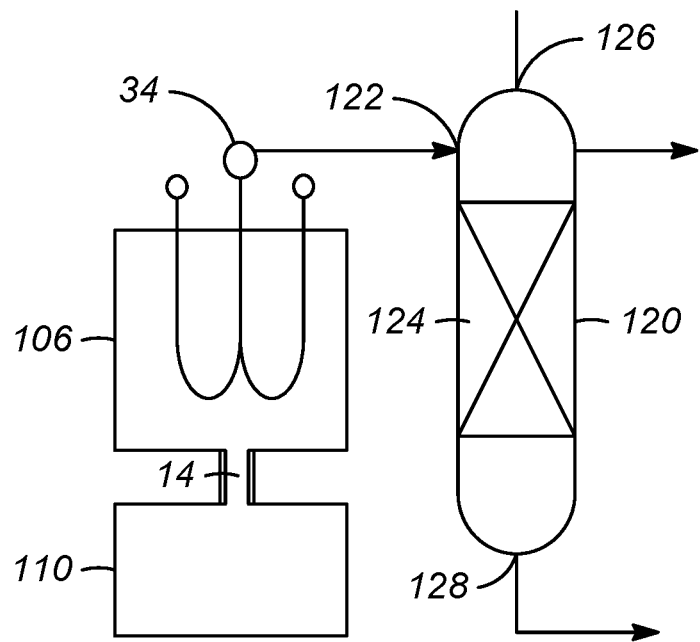
FIG. 2 is a layout of a fired heater, a reactor, and a convection bank.

In one embodiment of the present invention, as shown in FIG. 2, the fired heater 100 positioned above a convection bank 110. In this configuration, the fired heater 100 can be raised and to elevate the outlet manifold 34. The heater can be elevated to be proximate to the inlet 122 of a reactor 120. In this embodiment, the heater elevation is dependent on the height at which the reactor inlet is positioned. This design allows for retrofitting of existing reactors having inlets at the top of the reactor 120 without having to add substantial transfer piping, or without having to replace a reactor unit. An existing moving bed reactor can have a process stream inlet located above the reactor moving bed 124, a catalyst inlet 126 at the top of the reactor, a catalyst collector at the bottom of the reactor, and a process fluid outlet. The catalyst collector 130 has a catalyst outlet 128 at the bottom of the catalyst collector. With a moving bed reactor, the moving bed of catalyst is in an annular region and the catalyst flows down through the annular region. The process fluid enters the reactor on one side of the annular region, flows across the annular reactor bed, and out the other side of the annular region.

For this fired heater design, the fired heater can be elevated to keep the process fluid outlet with 2 meters of the elevation of the reactor inlet. Preferably the elevation differences of the manifold and the reactor inlet can be made smaller and can be reduced to 1 m, or even 0.3 m.

In another embodiment, the convection bank 110 can be positioned to the side of the fired heater 100 when there is insufficient space below the fired heater to position the convection bank below the fired heater.

Figure 3:
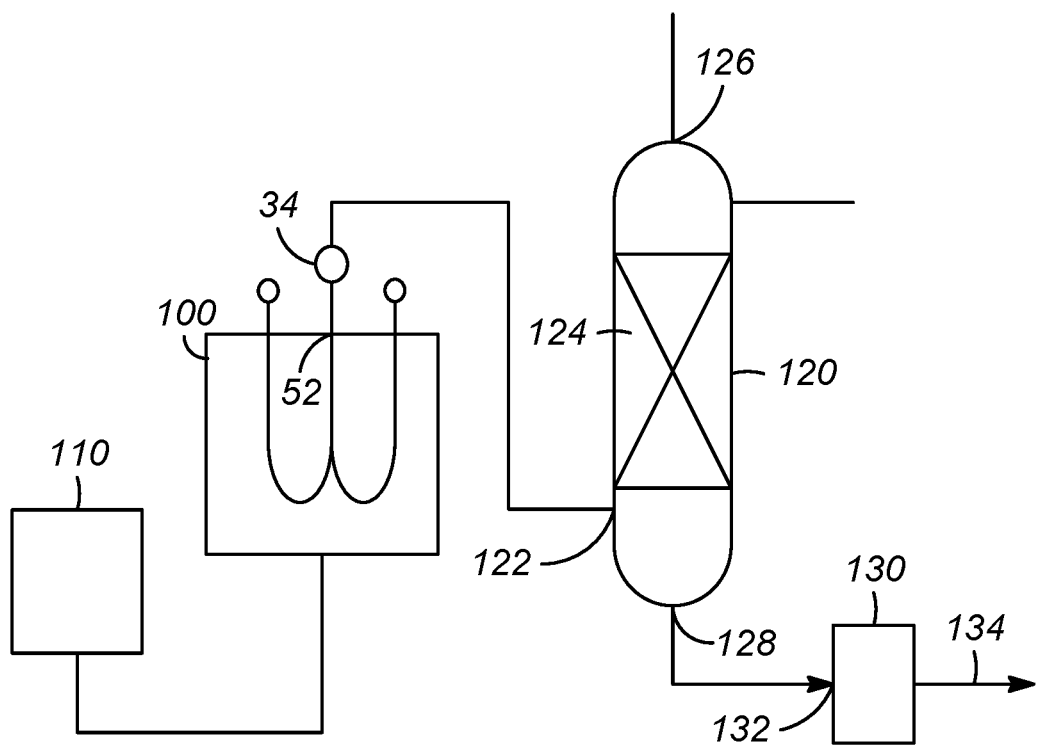
FIG. 3 is an alternate layout of a fired heater, a reactor, and a convection bank.

In another embodiment, as shown in FIG. 3, an existing reactor 120 has an inlet located below the reactor moving bed 124. The moving bed reactor 120 includes a process stream inlet 122, a catalyst inlet 126, and a catalyst outlet 128 at the bottom of the reactor 120. This embodiment includes a catalyst collector 130 having an inlet 132 in fluid communication with the catalyst outlet 128 and a catalyst collector outlet 134. In this embodiment, the fired heater 100 is on or near grade and the outlet manifold has a lower elevation, the reactor 120 can be elevated to provide for the process coil outlet 52 to be located within 1 m elevation of the reactor process fluid inlet 122. In this embodiment, the reactor elevation is dependent on the height where the heater outlet manifold is positioned.

The W-tube process coil reduces the thermal cracking and capital cost of the fired heaters. The smaller fired heater allows for better positioning of the fired heater relative to the reactor and to minimize transfer line lengths between the fired heater and reactor. This reduces the hot residence time in the transfer lines and reduces thermal cracking in the transfer lines.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. An apparatus for reducing hot transfer line volume, comprising:
    a radiant fired heater having a single cell, at least one process coil having one process coil outlet port and two process coil inlet ports, burners, and a flue gas outlet;
    at least one outlet manifold having an inlet in fluid communication with the process coil outlet port; and
    a moving bed reactor having a process stream inlet located above the reactor moving bed, a process fluid outlet, a catalyst inlet, a catalyst collector at the bottom of the moving bed reactor, and a catalyst outlet at the bottom of the catalyst collector, said moving bed reactor is connected to said at least one outlet manifold for carrying process fluid to said moving bed reactor via said hot transfer line;
    wherein each process coil has a configuration of three tubes in a parallel orientation, with two semi-circular tubular sections connecting the ends of the tubes, such that the tubes and tubular sections form a generalized W-shaped coil, with the central tube having one end connected to the outlet port, and the two outer tubes having one end connected to an inlet port.

2. The apparatus of claim 1 further comprising a convection bank having an inlet in fluid communication with the flue gas outlet, and heating tubes, wherein the heating tubes have an inlet and an outlet.

3. The apparatus of claim 2, wherein the convection bank is above or below the fired heater.

4. The apparatus of claim 2, wherein the convection bank is positioned to the side of the fired heater.

5. The apparatus of claim 2, wherein the heating tubes are for steam generation.

6. The apparatus of claim 1, wherein the radiant fired heater is elevated to provide for that the moving bed reactor process stream inlet is located within 0.3 m elevation of the outlet manifold outlet.

7. The apparatus of claim 1 further comprising:
    a moving bed reactor having a process stream inlet disposed located below the reactor moving bed, a process fluid outlet, a catalyst inlet, and a catalyst outlet at the bottom of the reactor; and
    a catalyst collector having an inlet in fluid communication with the reactor catalyst outlet and a catalyst collector outlet.

8. The apparatus of claim 7 wherein the moving bed reactor is elevated to have the process stream inlet located within 1 m elevation of the manifold outlet.

9. The apparatus of claim 7, wherein the moving bed reactor is elevated to have the process stream inlet located within 2 m elevation of the manifold outlet.

10. The apparatus of claim 7 further comprising a convection bank having an inlet in fluid communication with the flue gas outlet, and heating tubes, wherein the heating tubes have an inlet and an outlet.

11. The apparatus of claim 10, wherein the convection bank is on top of the fired heater.

12. The apparatus of claim 10, wherein the convection bank is positioned to the side of the fired heater.

13. An apparatus integrated with a reactor, comprising:
    a moving bed reactor having a process stream inlet located at a designed elevation, a process fluid outlet, a catalyst inlet, a catalyst collector at the bottom of the reactor, and a catalyst outlet at the bottom of the catalyst collector, wherein the process stream inlet is located above said moving bed reactor;
    a fired heater having at least one process coil, and a flue gas outlet, wherein the process coil has at least one inlet and one outlet, and wherein the process coil outlet is located within 1 m elevation of the moving bed reactor process stream inlet designed elevation; and
    at least one outlet manifold and a transfer line, said at least one outlet manifold is in fluid communication with said fired heater and at least one outlet manifold is connected to said moving bed reactor for carrying process fluid to said moving bed reactor via said hot transfer line.

14. The apparatus of claim 13 further comprising a convection bank having an inlet in fluid communication with the fired heater flue gas outlet, wherein the convection bank comprises heating tubes having an inlet and an outlet.

15. The apparatus of claim 13 further comprising said outlet manifold having multiple inlets with each inlet in fluid communication with a process coil outlet, and an outlet in fluid communication with the moving bed reactor process stream inlet, and wherein the manifold outlet is located at an elevation within 0.3 m of the moving bed reactor process stream inlet.

16. The apparatus of claim 14 wherein the convection bank is located below the fired heater, or to the side of the fired heater.

17. An apparatus integrated with a reactor, comprising:
a moving bed reactor having a process stream inlet located at a designed elevation, a process fluid outlet, a catalyst inlet, and a catalyst outlet at the bottom of the moving bed reactor, wherein the process stream inlet is located below the moving bed reactor;
a catalyst collector having an inlet in fluid communication with said catalyst outlet at the bottom of the moving bed reactor and a catalyst collector outlet; and
a fired heater having at least one process coil, and a flue gas outlet, wherein the process coil has at least one process coil inlet and at least one process coil outlet, and wherein the at least one process coil outlet is located within 1 m elevation of the moving bed reactor.

18. The apparatus of claim 17 further comprising an outlet manifold having multiple inlets with each inlet in fluid communication with a process coil outlet, and an outlet in fluid communication with the moving bed reactor process stream inlet, and wherein the manifold outlet is located at an elevation within 0.3 m of the moving bed reactor process stream inlet.

19. The apparatus of claim 17 further comprising a convection bank having an inlet in fluid communication with the fired heater flue gas outlet, wherein the convection bank comprises heating tubes having an inlet and an outlet.

\* \* \* \* \*